(12) United States Patent
Nebosis et al.

(10) Patent No.: US 11,051,784 B2
(45) Date of Patent: **\*Jul. 6, 2021**

(54) METHOD AND SYSTEM FOR DETERMINING THE POSITION OF A PORTABLE IMAGE DETECTOR ASSEMBLY WITH RESPECT TO AN EMISSION POINT OF AN X-RAY SOURCE IN A RADIOGRAPHIC SYSTEM

(71) Applicant: AGFA NV, Mortsel (BE)

(72) Inventors: Rainer Nebosis, Munich (DE); Roland Reuter, Munich (DE)

(73) Assignee: AGFA NV, Mortsel (BE)

( \* ) Notice: Subject to any disclaimer, the term of this patent is extended or adjusted under 35 U.S.C. 154(b) by 0 days.

This patent is subject to a terminal disclaimer.

(21) Appl. No.: 16/497,456

(22) PCT Filed: Mar. 28, 2018

(86) PCT No.: PCT/EP2018/057856
§ 371 (c)(1),
(2) Date: Sep. 25, 2019

(87) PCT Pub. No.: WO2018/184923
PCT Pub. Date: Oct. 11, 2018

(65) Prior Publication Data
US 2020/0107798 A1    Apr. 9, 2020

(30) Foreign Application Priority Data
Apr. 7, 2017 (EP) .................................. 17165497

(51) Int. Cl.
*A61B 6/00* (2006.01)

(52) U.S. Cl.
CPC ............ *A61B 6/588* (2013.01); *A61B 6/4405* (2013.01); *A61B 6/4452* (2013.01); *A61B 6/547* (2013.01);
(Continued)

(58) Field of Classification Search
CPC ......... A61B 6/00; A61B 6/547; A61B 6/4405; A61B 6/588; A61B 6/587; A61B 6/4452;
(Continued)

(56) References Cited

U.S. PATENT DOCUMENTS

2006/0109958 A1\* 5/2006 Ertel ...................... A61B 6/587
                                                                378/205
2009/0032744 A1   2/2009 Kito et al.
(Continued)

FOREIGN PATENT DOCUMENTS

DE    10 2010 008 551 A1   8/2011
WO        2013/162762 A1   10/2013

OTHER PUBLICATIONS

Official Communication issued in International Patent Application No. PCT/EP2018/057856, dated Jul. 24, 2018.
(Continued)

*Primary Examiner* — Jurie Yun
(74) *Attorney, Agent, or Firm* — Stinson LLP

(57) ABSTRACT

A method and system for accurately localizing a wireless radiographic detector in a radiography system, based on a method to accurately determine distances between a set of generator arrays and sensor arrays. The generator arrays and sensor arrays are preferably orthogonally arranged magnetic field generators and sensors, that allow measurements of distances without being affected by presence of human tissue between the generator and sensor arrays.

14 Claims, 5 Drawing Sheets

(52) U.S. Cl.
CPC ...... *A61B 6/587* (2013.01); *A61B 2562/0223* (2013.01)

(58) Field of Classification Search
CPC ......... A61B 6/0492; A61B 6/58; A61B 6/585; A61B 6/1049; A61B 6/54; A61B 6/542
See application file for complete search history.

(56) References Cited

U.S. PATENT DOCUMENTS

2012/0230473 A1    9/2012  Stagnitto et al.
2019/0125285 A1*   5/2019  Nebosis ................. A61B 6/467

OTHER PUBLICATIONS

Nebosis et al., "Method and System for Determining the SID and the Thickness of a Patient in a Radiographic System", U.S. Appl. No. 16/497,457, filed Sep. 25, 2019.

* cited by examiner

METHOD AND SYSTEM FOR DETERMINING THE POSITION OF A PORTABLE IMAGE DETECTOR ASSEMBLY WITH RESPECT TO AN EMISSION POINT OF AN X-RAY SOURCE IN A RADIOGRAPHIC SYSTEM

CROSS REFERENCE TO RELATED APPLICATIONS

This application is a 371 National Stage Application of PCT/EP2018/057856, filed Mar. 28, 2018. This application claims the benefit of European Application No. 17165497.3, filed Apr. 7, 2017, which is incorporated by reference herein in its entirety.

BACKGROUND OF THE INVENTION

1. Field of the Invention

The invention generally relates to the localization of the position of a radiographic detector in a radiography system and more specifically to mobile radiography systems, wherein a preferably wireless image detector is positioned behind the object to be imaged, but of which the exact position is not always accurately known. An accurate determination of the position of the image detector in relation to the X-ray source is important for determining the imaging parameters, the tube and patient positioning.

2. Description of the Related Art

It has been a longstanding problem in conventional radiography to accurately determine all parameters of the acquisition geometry of a particular radiography system applied to a particular exposure setup. In conventional radiography, the beam of an X-ray source (in most cases an X-ray tube) is modified or shaped to optimally expose the patient tissue subject to examination to render an optimal image quality result, while minimizing the patient exposure to radiation. The part of the X-ray beam exposing the region of interest of a patient is partially attenuated by the tissue encountered by the beam on its path to the imaging detector, and forms a latent image that is accumulated (CR-image) or integrated (DR-image) in a detector sensitive to X-rays. So-called exposure settings fully determine the quality of the X-ray beam and have an important impact on the resulting image. The exposure settings are essentially determined by the type of exam to be carried out, and depend on the following: type of examination (soft tissue examination require different settings than the examination of bony structures), age of the patient (pediatric or not), specific acquisition geometry SDD (source detector distance), ODD (object detector distance) and incidence angle of the beam) and thickness of the patient. The exposure settings are defined in terms of mA (electric current passed through the anode of the X-ray tube), s (exposure duration in seconds), and kV (tube voltage in kilo-volts).

In fixed radiography installations, the acquisition geometry is relatively easy to be determined since the degrees of freedom of the movements of the different modality components are defined by the modality design and the movements of the individual components can be easily tracked by measuring their displacements. The exact locations in space of the main determining components for the acquisition geometry (namely the X-ray source, the image detector and table surface) can be relatively easily calculated by tracking or measuring the movements of those components relative to reference positions. Digital readings of the displacements or rotations of a C-arm gantry can unambiguously define the emission point and inclination angle of the X-ray beam, for instance. In a typical fixed radiography installation, also the location of the image detector can be unambiguously located because of the fact that it resides in a so-called detector "bucky" of which the location in the table is predetermined or can be easily measured.

The situation is different for older radiography equipment that don't have digital position readings on all the components, and also for mobile radiography devices or for examination types which require the detector to be outside the bucky. Mobile X-ray devices are used as a versatile solution for acquiring radiography images under circumstances where a patient cannot be easily transported to a dedicated X-ray room, or cannot be positioned easily. Mobile X-ray devices are used in emergency rooms, in interventional setups, or in cases where the patient needs an examination in his hospital bed. It is clear that under these circumstances it is a lot less obvious to accurately determine the acquisition geometry when the relative position information between the different components, such as the X-ray source and the image detector, is not available.

Especially, the determination of the exact position and orientation of an image detector relative to the X-ray source is challenging since the two objects typically do not have a mechanical relationship, and may even not be in a line of sight of each other. One has to assume that the object or patient to be imaged obscures the image detector when looking from the source perspective. Therefore, distance-measuring techniques that require a clear line of sight cannot be applied. In the art, different distance measuring techniques relying on a variety of effects have been proposed as a solution. Some of the solutions rely partly or entirely on the integration of kinetic sensors, which can record and calculate displacements based on the acceleration measurements, or angulations with respect to—for instance—the gravity force. These solutions require complex calculations of the recorded movements and are not sufficiently accurate for the application described here as the sensor may drift over time. A solution based on this principle also always requires a calibration step, into which the object to be tracked has to be registered in a reference position. Additionally, the type of kinetic sensors used in this kind of application have certain intrinsic limitations that do not allow certain parameters to be measured. For instance, acceleration sensors are not able to detect a rotation of an object oriented in plane parallel with the ground surface (perpendicular to the force of gravity). As an example, US patent US2014376700 (Samsung Electronics Co. Ltd.) proposes a solution to align at least the orientations of the X-ray tube and the detector using such angle measurement sensors.

In the same disclosure, also magnetic field sensors are proposed to measure and detect a relative position of an X-ray image detector (to which they are attached) relative to a magnetic field generator which is connected to an X-ray source assembly. The magnetic field generator generates a static magnetic field, of which the intensity is measured at the positions of the magnetic field sensors and brought in relation with the relative distances between the magnetic field sensors and the magnetic field generator (the latter is positioned close to the X-ray source). The magnetic field is approximately inversely proportional to the third power of the respective distance between the magnetic field generator and the individual magnetic sensors. The measured magnetic field intensity values are thus indicative of the distances between the magnetic field generator and the magnetic sensor. The magnetic field measurements are used in combination with the acceleration sensors in order to obtain a relative location and relative orientation of an image detector, which allow, in combination with the determination of a start location, to calculate absolute distances from the X-ray source position. This solution is however not very accurate, and is very susceptible to external influences which may influence the magnetic field such as the presence of metallic objects or the presence of other static or non-static magnetic fields, such as the earth's magnetic field or the presence of electromagnets or coils in the vicinity of the detectors.

U.S. Pat. No. 9,179,886 (Carestream Health, Inc.) discloses an approach whereby a method for alignment of an image detector with the beam of an X-ray source is also based on magnetic principles. In the disclosure, a time-varying magnetic field pattern is generated at a position connected to the X-ray source, so that this signal can be picked up and measured by a number of magnetic sensors (at least 2) which are connected to the imaging detector. The magnetic field pattern is generated at a pre-determined frequency chosen so that the signal is made transparent for human tissue (i.e. that the energy is not absorbed by human tissue). The advantage of the alternating magnetic field is that the amplitude measurements allow to compensate for any present static magnetic fields such as the earth's magnetic field. The time-varying signal is picked up and measured at multiple spatially distributed magnetic sensor elements (or coils) which are arranged at fixed positions of an image detector, and of which the combined read-outs induced by the generated magnetic field are indicative for the location of the detector in relation to the magnetic field generator. The technique is thus an improvement over the previously mentioned solution in that it is less susceptible to external magnetic disturbances, but at the same time, it is clear that the technique does not intend (and does not achieve) to obtain absolute location measurements of the sensors attached to the detector. The disclosure achieves a more reliable estimation of the relative positions of all detectors in relation to the magnetic field generator. By comparing the measured values against a set of reference values, the method is capable of providing an indication of the alignment of the image detector with the X-ray source location.

An important aspect that contributes to the accuracy of the system is that the different magnetic sensors are differently aligned, although only in the same plane as the image detector. At least two magnetic sensors are required, and are preferably aligned under at least 45° of each other. Additional magnetic sensors may be added to further improve the accuracy of the method. Additional detectors are preferably arranged in the same plane but under different offset angles.

In another disclosure (U.S. Pat. No. 7,581,885) the idea of using a set of 3 GPS sensors built into the corners of an encasement of an imaging detector is used to perform the absolute GPS-localization of the 3 sensors (measurements which rely on triangulation techniques for determining the individual position of the GPS sensors), using the satellites of the GPS. In the document, the idea is raised that once the exact locations of the 3 sensors in the corners of the imaging detector are known, also the relative position of the imaging detector with respect to the X-ray source can be calculated. Today, it is however generally known that the accuracy of the (civil) GPS is insufficient for this intended application of locating an object on the sub-centimeter level, as the standard horizontal accuracy of a civil GPS receiver under optimal signal receiving conditions is 3.5 meters. The most optimized GPS location enhancement techniques (such as RKP used in the mining industry) result in an accuracy of 4 cm. Especially when it is generally known that many external factors can degrade the GPS positioning accuracy (such as signal blockage in buildings, or signal reflections against walls), it is clear that the accuracy of the proposed system will especially suffer under the operating conditions of such an X-ray imaging detector alignment system; namely inside a hospital building.

In summary, a number of solutions have been described in the art which at best resolve one of the partial problems encountered when looking out for a full and accurate solution to determine the position and orientation of an image sensor with respect to the position of an X-ray source. Many good and accurate solutions exist in case that direct line-of-sight distance measurement techniques can be used, but only partial solutions exist when the visual path between the source and the detector is blocked. The most promising techniques evading the direct-line-of-sight limitation are based on magnetic field measurement techniques, but so far, only estimations or relative measurements with limited accuracy and reliability have been achieved.

SUMMARY OF THE INVENTION

The invention provides a method for determining the relative position of a portable image detector assembly with respect to an X-ray source configuration in a radiographic system, the method comprising the steps of generating a time dependent sequence of orthogonally arranged alternating magnetic fields in at least 3 spatially distributed generator arrays which are connected to said X-ray source, measuring the signals induced by said sequence of (9) alternating magnetic fields in at least 3 detector sets each consisting of an orthogonally arranged magneto meter triplet, said detector sets being spatially associated with said portable image detector assembly, calculating (9) absolute distances from each generator array to each detector set based on field strength information only, and obtain coordinate data for each detector set by performing trilateration on said (9) absolute distances.

It is an object of this invention to resolve the above mentioned problems, and provide a system which allows accurate and reliable positioning of an image detector with respect to the position and orientation of an X-ray source in a radiography system.

In order to resolve the longstanding problem in radiography of identifying in a reliable way the location and orientation of an imaging detector with respect to the position and orientation of an X-ray beam, it is necessary to be able to find a technique which allows to determine all 6 degrees of freedom that can determine said position and orientation. While other techniques, referred to above, are limited to 4 or 5 degrees of freedom (because they rely on partially relative measurement techniques such as angle measurements or alike), our invention resolves this limitation by determining the actual spatial coordinates (x, y, z) of three known points in the imaging detector. These three known points refer to the physical locations of three sensors of which the exact location is determined by the method of this invention. These three points mathematically define a plane in which the image detector is oriented. But also they define the rotation angle of the image detector about all axes, and the distances from the reference point located on the X-ray source assembly. Knowing the three coordinates for the three sensors determines the 6 degrees of freedom of the position of the imaging detector in space relative to a reference coordinate system determined by the location of three signal generators attached to the X-ray source assembly.

The accurate determination of the image detector with respect to the orientation of the X-ray beam, allows then different practical applications in radiography, such as an automated and accurate determination of the SID (source image distance) which is an important parameter to select the exposure settings for any type of radiography study. Orientation and position data allow automated or guided adjustment of the alignment of the detector (and patient) with the X-ray beam. Another application can be found in the automatic determination of the acquisition geometry of a radiography system in a tomosynthesis context, wherein an accurate knowledge of the acquisition geometry is necessary for accurate image reconstruction.

The actual determination of the spatial coordinates (x, y, z) of the three signal sensors in the imaging detector is based on a known calculation technique used in the field of GPS; namely trilateration. The method relies on reliable measurements of the distances between at least three signal generators (the satellites in GPS context) and a signal sensor. In the assumption that the exact location of the three signal generators is known, then also the exact location of the signal sensor registering the at least three signals from said three signal generators can be derived through this triangulation calculation. The key to the calculation are the reliable measurements of said distances.

In the context of this invention, the measured signals are indicative of the absolute distance between a signal generator and a signal sensor, which means that every measured signal is directly related to an absolute distance (in a linear or non-linear fashion). Different measurement techniques or physical principles may be envisaged allowing direct derivation of an absolute distance from a measured signal. Examples may be for instance, the measurement of an acoustic echo-signal, a radar signal, a laser distance measurement, magnetic field strength, or alike.

In the context of this invention, a signal generator consisting of a triplet of orthogonally arranged coils is called a generator array. Similarly, a signal sensor consisting of a triplet of orthogonally arranged coils is called a sensor array.

DETAILED DESCRIPTION OF THE PREFERRED EMBODIMENTS

Figure 1:
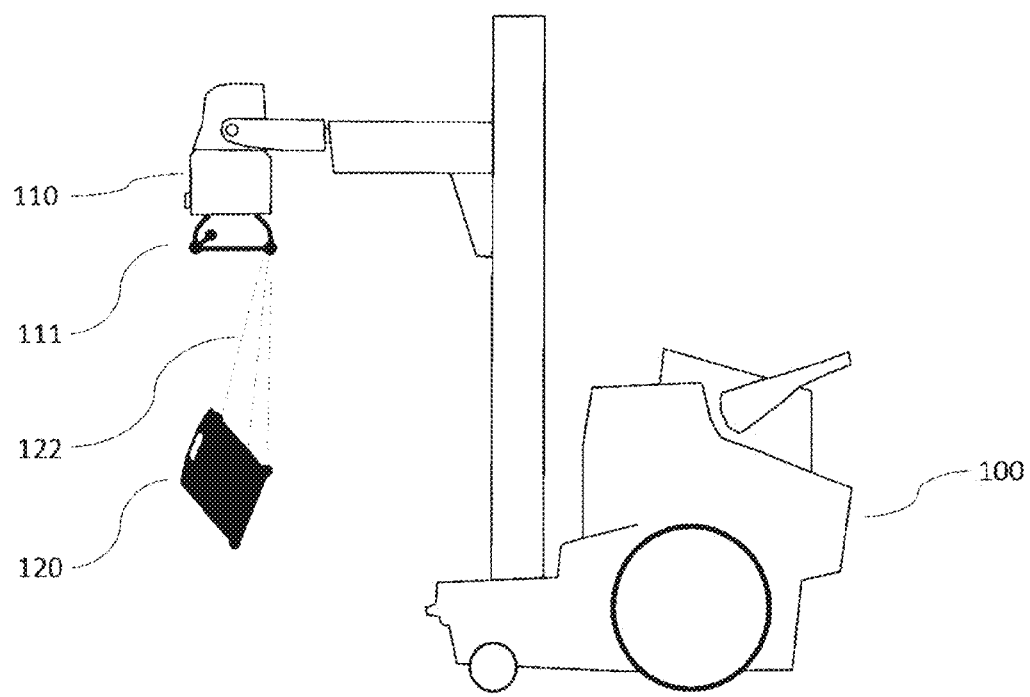
FIG. 1 shows a schematic representation of a mobile X-ray device [100] to which a set of 3 generator arrays [111] is attached by means of a structure that is fixed to the X-ray source assembly or collimator [110]. The 3 generator arrays are fixed in a frame-like structure which keeps the generator arrays at a fixed distance from each other, and of which the dimensions are known. The image detector assembly [120] is shown in conjunction with the X-ray device. A signal [122] is sent from one of the generator arrays, and is detected by all 3 sensor arrays which are integrated into or attached to the image detector assembly [120].
Figure 2:
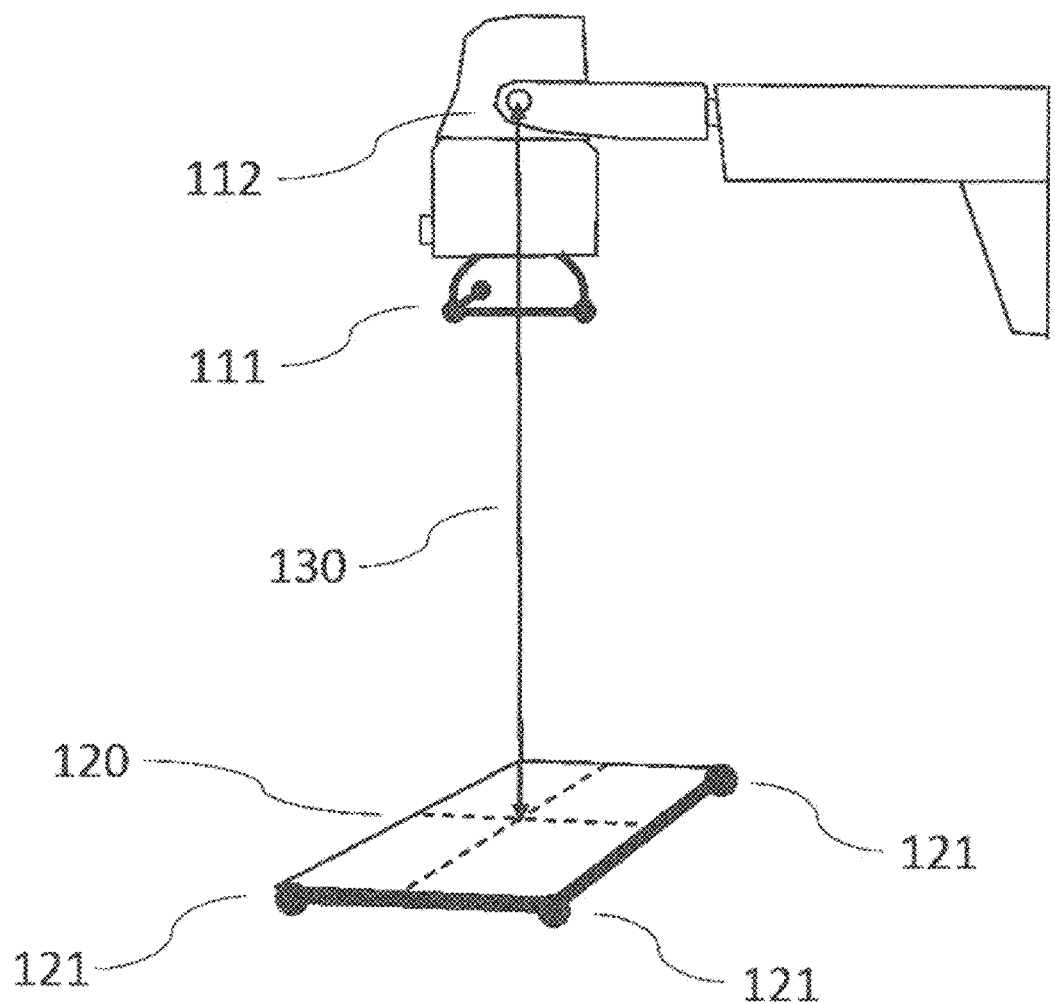
FIG. 2 shows a details of the X-ray source assembly to which the set of 3 generator arrays [111] is attached. The detector arrays are spaced from each other. The arrow [130] represents the SID (source to image detector distance) and can be obtained through measurements performed by the method of the invention. The SID is the distance between the center of the image detector assembly [120] and the emission point [112] of the X-ray source.
Figure 3:
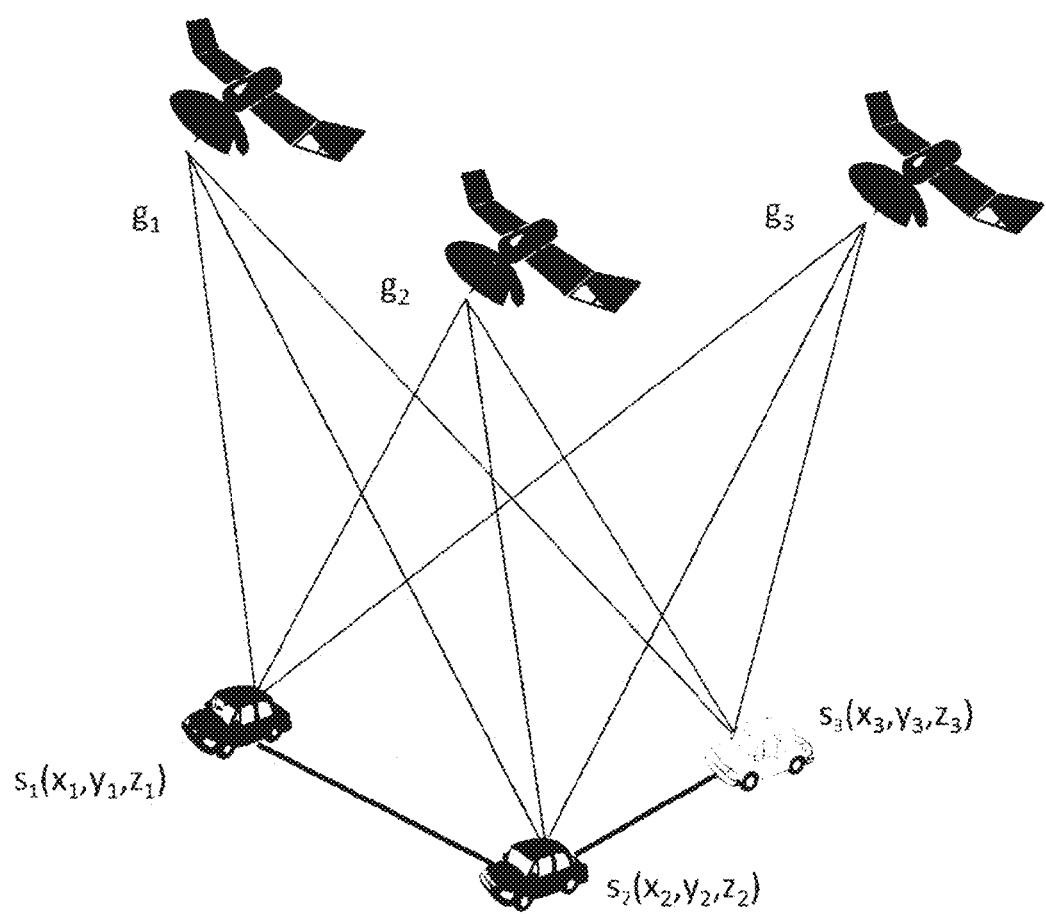
FIG. 3 shows the concept of trilateration which is also applied in GPS technology, which allows to accurately calculate the coordinates of a GPS-receiver (represented by one of the cars in the picture) under the minimum condition 3 satellites send a signal that allows the GPS-receiver to determine its distance to all of the 3 satellites. The minimum requirement to apply this technique is to have at least 3 satellites providing the distance information. In our invention, the GPS-satellites are replaced with generator arrays that each provide a consecutive signal to each of the sensor arrays (in analogy with the cars in the figure) that can be interpreted by the sensors as their respective distance to the generator array. In the invention, all sensor arrays (cars) calculate their distances to the 3 generator arrays (satellites), after which 3 trilateration calculations are executed to obtain the coordinates from the sensor arrays (cars): (x1,y1,z1), (x2,y2,z2) and (x3,y3,z3).
Figure 4:
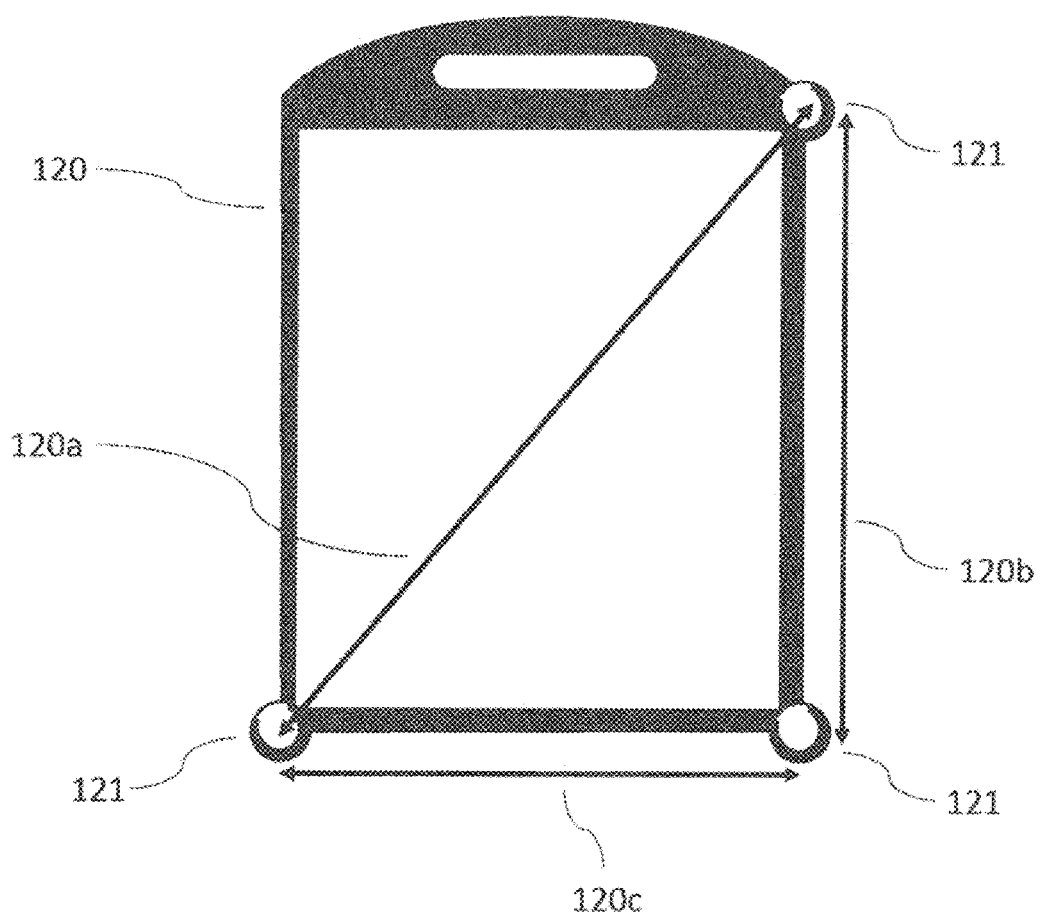
FIG. 4 shows an embodiment of an X-ray detector assembly [120] which on 3 of its corners is foreseen with a sensor array [121]. In this configuration, it is obvious that the internal distances between the sensor arrays [120a], [120b] and [120c] are constant and known, and therefore can be used to verify the accuracy of the obtained sensor array coordinates via the method of this invention.
Figure 5:
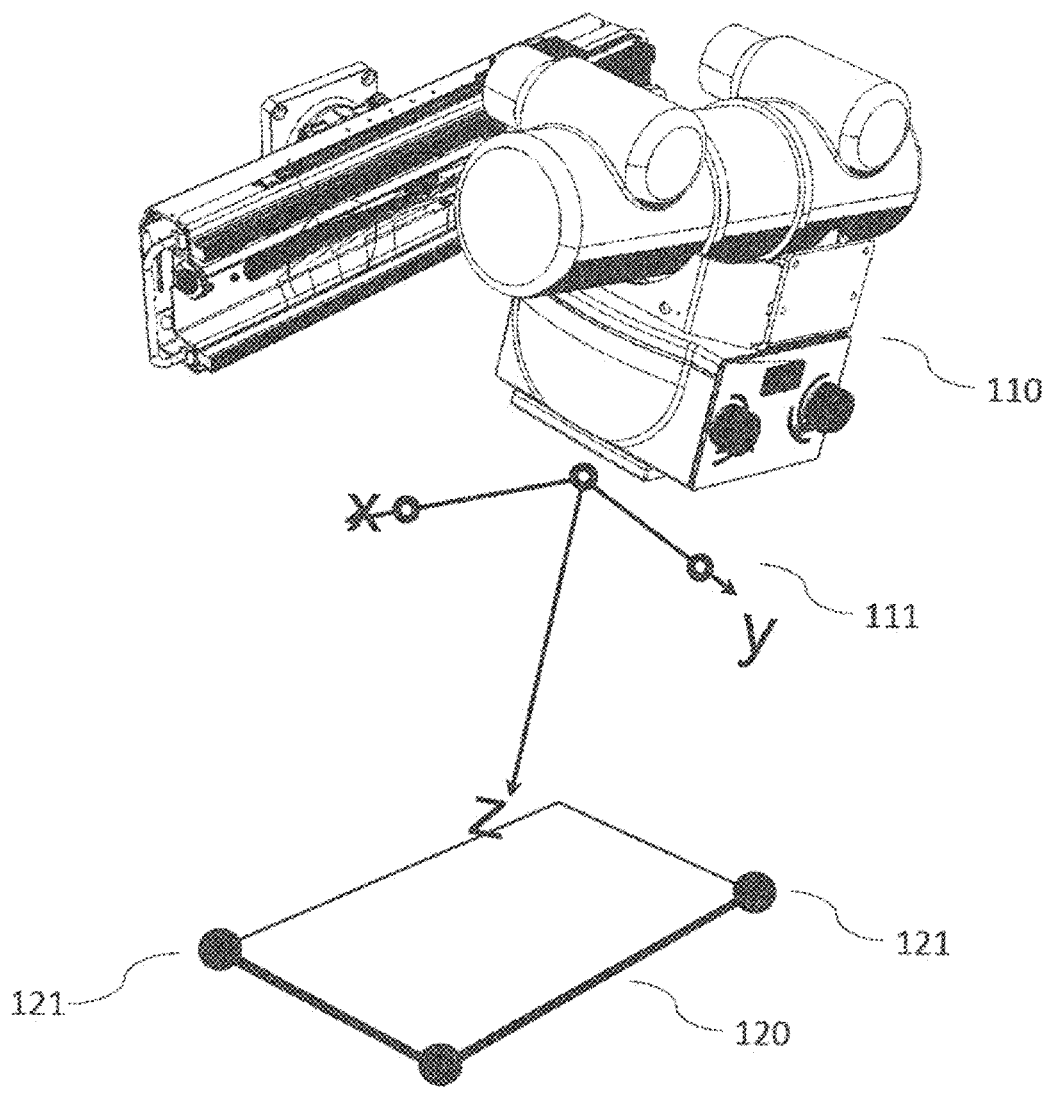
FIG. 5 shows an embodiment of a collimator [110] aligned with a set of generator arrays [111] which are associating their configuration in space with the alignment of the X-ray beam (represented by the Z-axis indicated in the figure).

A first embodiment of this invention is based on the use of a set of at least three signal generators, which are physically connected to an X-ray source assembly of a radiography system. The at least three signal generators are mechanically fixed to the X-ray source assembly in order to fix a reference coordinate system in space which is selected as the point from where the X-ray radiation originates and that determines the orientation of the X-ray beam. This virtual point is called the emission point of the X-ray source. At least three signal generators are required to determine the location and orientation of the reference coordinate system. Adding more signal generator elements may contribute to a better accuracy of the system, but is strictly speaking not required. The at least three signal generators are so arranged that they are spatially separated from each other (for instance located at positions around the X-ray source assembly) so to ensure that their generated signals appear to be different for detectors at different positions.

In a preferred embodiment, three signal generators sequentially or successively generate their signal, meaning that the generators are never operated simultaneously, but one after the other. The sequential or successive signal sequence is then repeated until the detector position measurements are completed.

The particular aspect or characteristic of the generated signal that determines the absolute distance between the signal sensor location and the generator location is then picked up by signal sensors within detection range of the signal generators. A prerequisite for a signal generation and sensing technology to be used in this application is that at least one measureable parameter of the signal (such as the intensity, the amplitude or signal strength) should be dependent on the physical distance between the signal generator and the signal sensor itself. It is conceivable and acceptable that additional mathematical operations and calibrations are required to convert the signal data into a distance value.

Preferably, the measurable parameter of the signal should not be easily influenced or degraded by environmental factors, and should be transparent for human tissue.

Further to our preferred embodiment above, there are three signal sensors built into the image detector assembly, of which the position is being detected. At least three of the above mentioned signal sensors are required for the invention to work, and they are required to be as far as possible spatially separated from each other to obtain the most accurate results. An obvious design choice for the location of the three signal sensors in an image detector assembly would be in three of four corners of the assembly frame. Since the determination of the exact positions of the three signal sensors is the purpose of the method of this invention, it is clear that these three positions can uniquely identify the location and orientation of the image detector assembly when the dimensions of the image sensor assembly and the locations of the signal sensors within the assembly are known. In geometry, two points identify a line in space, three points define a plane. The invention therefore requires at least three signal sensors, which completely define the position and orientation of the image sensor assembly, while every additional sensor may only contribute to an increased accuracy of the calculation. Moreover in the case that the internal distances between the signal sensors (or the dimensions of the image detector assembly) are known, the accuracy of the measured signal sensor locations of the three signal sensors can be verified by comparing the known internal distances of the sensors against the measured internal distances resulting from the measured locations of the signal sensors.

The three signal generators produce a continuously cycling time-based generator signal sequence so that all possible distance measurements (consisting of three simultaneous measurements between the active signal generator and the three signal sensors) can be performed one after another. As explained above, the location of the signal sensor determines the measured signal value which is picked up by each signal sensor for every generator signal. This results in our particular embodiment in a total of nine signal measurements. These measured values are then converted into distance measurements, and fed into a trilateration algorithm which calculates the 3D-coordinates of the positions of the signal sensors relative to the position of the (virtual) emission point.

The trilateration algorithm is a known mathematical method that essentially identifies the point in space that intersects with three (imaginary) spheres (in the case of our embodiment spheres around the three signal generators) defined by the positions of the signal generators as the center of said spheres and the above mentioned calculated distances as their respective sphere radii. In theory, the results of this equation are 2 points in space, of which one can be easily ruled out since the only valid one should be found in the direction of the X-ray beam, while the other is mirrored through the emission point towards the rear of the X-ray source assembly (and thus away from the X-ray beam direction).

As explained above, this means that in case that any additional signal generators are added to the system (so that there are more than three generators in total), the resulting distance measurements to the different signal sensors will contribute to the accuracy of the calculation of the coordinates by adding a supplementary sphere whose surface should also mathematically intersect with the coordinate point of the signal sensor. In case that the additional sphere does not exactly intersect with the location of the signal sensor calculated from the first 3 spheres, then this data can be used to interpolate between the different possible solutions (or other optimization algorithms know from GPS technology can be used).

A further important aspect of the invention is the appropriate choice of distance detection principle that can fulfill the above-mentioned requirements of accuracy and transparency to human tissue. A promising starting point appears to be magnetism, as it is known that magnetic fields pass through non-metallic objects. Nevertheless, other pervasive waves, beams or radiating energies may be considered as alternatives. It is known in the art that the human body is transparent for alternating magnetic fields, on condition that the frequency is below 100 kHz. When the frequency raises above 5 MHz, human tissue starts to absorb a considerable fraction of the emitted energy and the signal becomes more sensitive for electromagnetic disturbances caused by electric circuits in the vicinity. These elements make frequencies above 5 MHz less usable for the purpose of distance measurement. The reason for using alternating magnetic fields as opposed to static magnetic fields is that this approach compensates for the presence of any static magnetic field, such as the earth's magnetic field in case that the amplitude of the received signal is taken as the parameter for distance measurement.

Therefore it is contemplated to use resonant magnetic signal generator- and sensor-pairs to optimize the magnet signal transfer to perform the distance measurements. In a preferred embodiment, the signal generator is a coil through which an alternating electric current is sent by an electronic generator circuit. The alternating electric current induces an alternating magnetic field of the same frequency which can be detected at a distance from the generator coil. A similar or smaller coil is used as the signal sensor and picks up the alternating magnetic field passing though it; inversely the alternating magnetic field induces an alternating current in the sensor coil that can be picked up and measured. The detector coil may be smaller in size and have a different winding number in comparison with the generator coil. The circuit that reads out the alternating electric current in the sensor coil is "tuned" to the frequency of the generator (hence the name "resonant") by means of the selection of the correct capacitor and resistor network, in order to optimize the sensitivity to the generator signal frequency.

While in the above preferred embodiment, the magnetic generator and resonant magnetic sensors are coils, different types of magnetic sensors may be used as alternatives, such as MEMS, Hall effect based sensors, magneto-resistive sensors, or alike . . . .

The amplitude of the measured alternating current in the resonant magnetic sensor has a relation with the distance between the signal generator and signal sensor. The amplitude is approximately inversely proportional to the cubic distance from the signal generated, when measured in radial direction from the generator. When the sensor coil is kept at the same distance to the generator but its orientation and/or the relative orientation is changed the received signal ranges from 100% to 0%.

$$L_m = \frac{const.}{R^3}(3(\hat{a}\cdot\hat{r})\cdot(\hat{r}\cdot\hat{b}) - \hat{a}\cdot\hat{b});$$

The mutual inductance $L_m$ depends on three vector products; a is a vector describing the orientation of the generator;

b describes the orientation of the sensor and r the relative orientation between sensor and generator.

The maximum amplitude can be measured when the vector determining the magnetic field in a certain position aligns with the sensor coil axis. In all other cases only the component of the magnetic field having the same direction as the sensor coil axis will contribute to the measured value in that particular sensor coil. Relying on the amplitude measurement for distance determination would only be a viable solution in the case that no angular variation could be expected (and this is not the case in our application).

Another aspect that influences distance measurement values based on the amplitude read-out from a single coil sensor are disturbances of the magnetic field, such as the presence of metallic objects in the vicinity of the sensor coil. Such disturbances have not so much an impact on the amplitude component of the magnetic field vector, but rather on the direction of the magnetic field vector. This means that such disturbances nevertheless can have a significant impact on the measured amplitude by the sensor coil in a certain position. This is another reason why relying on the amplitude measurement of a single magnetic sensor alone is not sufficient to determine the distance in a reliable way between sensor and generator.

Replacing the above described single coil (or other type of magnetic generator and sensor) structures in both the signal generator and signal sensor with a triplet of orthogonally arranged coils increases the distance measurement accuracy drastically, but only on condition that they are operated in a particular way which is disclosed in this invention. In the context of this invention, a signal generator consisting of a triplet of orthogonally arranged coils is called a generator array, and a signal sensor consisting of a triplet of orthogonally arranged coils is called a sensor array. While a single coil generator read out by a single coil sensor results in a single amplitude measurement, reading out all combinations of a generator triplet and a sensor coil triplet leads to 9 amplitude signal readouts, being 9 induced currents and resulting voltages $V_{i,j}$:

$$V_{m,n}^{ind} = \begin{bmatrix} v_{11} & v_{12} & v_{13} \\ v_{21} & v_{22} & v_{23} \\ v_{31} & v_{32} & v_{33} \end{bmatrix}$$

To simplify the calculation of distance and coordinates of the sensor array it is of advantage to square the voltage matrix elements and to define a signal matrix $S_{i,j}$ and the total signal $S_{tot}$ as well as the signal components $S_x$, $S_y$ & $S_z$:

$$S_{i,j} = \begin{bmatrix} v_{11}^2 & v_{12}^2 & v_{13}^2 \\ v_{21}^2 & v_{22}^2 & v_{23}^2 \\ v_{31}^2 & v_{32}^2 & v_{33}^2 \end{bmatrix}; S_{tot} = \sum_{i=1}^{3}\sum_{j=1}^{3} S_{i,j};$$

$$S_x = \sum_{i=1}^{3} S_{i,1}; S_y = \sum_{i=1}^{3} S_{i,2}; S_z = \sum_{i=1}^{3} S_{i,3};$$

The distance between the generator array and the sensor array R can be calculated from $S_{tot}$ and the axis intercepts or coordinates x; y & z from $S_x$; $S_y$ & $S_z$:

$$R = \sqrt[6]{\frac{6 \cdot const.^2}{S_{tot}}};$$

$$x = \frac{R^4}{const.} \cdot \sqrt{\frac{5 \cdot S_x - S_y - S_z}{18}};$$

$$y = \frac{R^4}{const.} \cdot \sqrt{\frac{5 \cdot S_y - S_x - S_z}{18}};$$

$$z = \frac{R^4}{const.} \cdot \sqrt{\frac{5 \cdot S_z - S_x - S_y}{18}};$$

It follows from the above formulas that it is possible to directly calculate the exact position (expressed in the coordinates x, y & z) of a sensor array. However, this method is not desirable for direct determination of the locations of the sensor array. The formulas above immediately illustrate that the determination of each coordinate is very sensitive to changes in the respective angle between the generator and detector coils.

In contrary to the sensitivity of the determination of the sensor coil coordinates through measurements of the magnetic signals as described above, the determination of the absolute distance R is not sensitive to the orientation of the sensor arrays with respect to the generator array; the distance R only depends on the summation of the signals generated in the coil triplet and picked up in the 3 sensor coils. It is upon this aspect that a reliable calculation of the absolute distance is based for further application in the trilateration method described above.

The distance measurement using the above mentioned set of coil triplets relies upon the sum of the squares of all voltage matrix elements. This measurement is surprisingly stable against external fields or disturbances induced by metal nearby as it uses all measured values (generated by all signal generators, and picked up by all signal detectors). The robustness can be explained by the fact that the distance is calculated from the complete magnetic field of all three emitter coils and not only from field components. Introducing a distance dependent gain matrix $G_{i,j}$ can compensate deviations from the simplified model used here which assumes that the distance R is many times larger than the size of the coils themselves, so that the coils may be assumed to behave like dipoles. The gain matrix can also correct for different coupling efficiencies between different receiver and generator coils. The measurement of the coordinate components x; y & z is less stable as only one receiver coil is used for each coordinate axis. Additionally there are different positions which produce the same voltage matrix—all locations that are point-symmetric to the emitter (which results in an uncertainty between 2 different possible solutions giving the same voltage matrix). But this problem is not important as for a radiography setup only half of the sphere is used—we always work in the same hemisphere, namely in the direction of the X-ray beam.

Electrical conductors such as metal plates or objects close to emitter or receiver produce interference and thus distort the measurement. This is caused by so-called "eddy currents" induced in the conductor by the alternating field of the emitter coils. The eddy currents in a conductor produce a magnetic field opposed to the inducing field. The magnetic field thus gets weaker (the eddy currents drain out energy from the magnetic field). On the other hand the eddy current also induce a current in the sensor coils. In case of resonate circuit design there is no phase difference between the directly induced currents and the eddy current induced currents. As a result, the measured (and thus observed) distance can get larger or smaller dependent on the location and orientation of the metal object. The impact on the measured distance depends on the distance of the conductor to the signal generator array or sensor array respectively. The influence on the x, y & z coordinates and the orientation of the sensor array is much larger than the distortion of the distance measurement when using the coil triplet configuration. The magnetic field induced in the conductor depends on the orientation of the conductor to the generator. Thus, the magnetic field is not reduced symmetrically but mainly in the direction perpendicular to the conductor so that the measured field strength is mainly changed for the sensor coil which is oriented almost perpendicular to the plate. In conclusion, eddy currents influence the distance measurement moderately (a slightly larger or smaller distance is measured) while coordinate and orientation measurements are influenced strongly.

Another potential source of distortion of the measurements are external alternating magnetic fields. Almost any electrical device produces alternating electrical fields in a wide frequency range. The influence of the fields strongly depends on their frequency and on the design of the read-out for the sensor coil. If the frequency of an external field fits the design frequency of any sensor coil the influence on the measurement accuracy can be very large. External magnetic fields may thus influence the measurement accuracy but the influence is less pronounced compared to eddy currents as the external field typically has no fixed phase relation or do not fit to the design frequency.

So, in conclusion, measuring absolute distances using magnetic field strength measurements can be made robust when using coil triplet configurations as alternating magnetic field generators and sensors for the above-mentioned reasons. In a preferred embodiment at least three of such alternating magnetic field signal generators (each consisting of an orthogonally arranged coil triplet) are used in combination with at least three such alternating magnetic field signal sensors (each also consisting of an orthogonally arranged coil triplet). As explained above, a reliable distance calculation can be made when for each generator array; alternating magnetic fields are generated successively in each of the 3 coils making up the triplet. These successive signals may be then read out be all sensor coils simultaneously of each signal sensor triplet or sensor array. Reading out the data from all respective sensor coil triplets results in the distance calculations between the generator coil triplet or generator array in question and the respective sensor coil triplets or sensor array. When the same process is repeated for all generator arrays (at least 3), an accurate calculation can be made based on the trilateration technique of the position of the image detector assembly in which the different sensor arrays are integrated.

It is important that the signal readout circuitry can identify the source (which source generator array and which coil in the array) from which the signal originates in order to ensure that the measured values (and thus the distances derived from it) are associated with the correct signal generator coil (or thus distance measurement). Another aspect with regards to synchronization between the generator and the measured sensor values is that it is important to know exactly when a new sequence starts so that the start and end of a signal phase can be accurately demarcated. Only when this can be achieved, can multiple measurement samples be taken accurately for the same assumed sequence.

In order to achieve this, various techniques may be applied such as for instance the transmittal of a synchronization signal indicating the start of a generator signal sequence as an electrical signal across an electrical connection from the generator coil driver circuitry, or as an encoded time-dependent signal embedded in the generator signal that can be detected wirelessly while reading out the signal sensor data. One of such exemplary signals may include a "blank phase" in the signal generator sequence during which no signal is generated in any of the signal generator coils. A predetermined threshold value transition will then determine the start and the end of the signal data phases.

One particular embodiment of this invention uses a method wherein a blank phase (wherein no signal is generated in any of the coils) is used as an encoded synchronization signal that marks the start of a full multi-coil (and even multi-triplet) generator sequence. A blank sequence is encoded into the successive coil generator sequence whereby the sum of the squares of the different measured signal sequences is used to calculate a reference threshold which marks the signal level below which the synchronization signal can be recognized. In fact, this reference threshold is calculated at 30% of this sum of squared signal levels. Every measured signal transition from below this reference threshold to above this reference threshold marks the start of the blank synchronization signal. This point in time can be used then to ensure that the read-out measurements are synchronized to the correct active signal generator coil, which induced the measured signal value.

This reference point can be measured for each sequence or a dedicated calibration cycle can be started at defined time intervals to synchronize the clocks of the sensor and generator circuits. In both cases, the sum of the squares of all induced signals in a single sensor array is used to determine the reference point. This can be done independently with each of the sensor arrays to ensure high reliability.

Moreover an additional test of the integrity of the reference point can be performed by using the expected form of the induced signals. Criteria for a reliable measurement (wherein n is number of generators) are the distance between two intersections is $1/(n+1)$ of cycle length or $3n/(3b+1)$ of cycle length, or alternatively the number of intersection points is $n+1$ or $n+2$.

The calculations involved in the execution of the method as explained in this invention may be carried out by means of standard computer equipment or a standard computer configuration, and may be embodied as a computer program, or alternatively may be embodied in a dedicated programmed circuit allowing to perform these calculations.

The invention claimed is:

1. A method for determining a relative position of a portable image detector assembly with respect to an emission point of an X-ray source in a radiographic system, the method comprising the steps of:

sequentially generating a signal in at least three spatially distributed signal generator arrays that are physically connected to the emission point of the X-ray source, each of the signal generator arrays comprising a triplet of orthogonally arranged coils;

simultaneously measuring the sequentially generated signals with at least three signal sensor arrays that are physically connected to the portable image detector assembly, each of the signal sensor arrays comprising a triplet of orthogonally arranged coils, the measured signals being indicative of absolute distances between the signal generator arrays and the signal sensor arrays, respectively; and obtaining coordinate data for a position of each of the signal sensor arrays by performing trilateration on the absolute distances between the signal generator arrays and the signal sensor arrays, respectively.

2. The method according to claim 1, wherein each of the signal generator arrays sequentially generates a sequence of orthogonally oriented alternating magnetic fields;
   each of the signal sensor arrays measures an orthogonal signal component $V_{i,j}$ of a magnetic field induced by each orthogonally oriented alternating magnetic field generated by the signal generator arrays; and
   a calculation of a distance Ri between one of the signal generator arrays and one of the signal sensor arrays is based on the measured values of all orthogonal signal components $V_{i,j}$ measured by the one of the signal sensor arrays and generated by the one of the signal generator arrays.

3. The method according to claim 2, wherein the distance Ri between the one of the signal generator arrays and the one of the signal sensor arrays is calculated as:

$$R_i = \sqrt[m]{\frac{const.}{S_{tot}}} \text{; wherein}$$

$$m = 6; S_{i,j} = \begin{bmatrix} v_{11}^2 & v_{12}^2 & v_{13}^2 \\ v_{21}^2 & v_{22}^2 & v_{23}^2 \\ v_{31}^2 & v_{32}^2 & v_{33}^2 \end{bmatrix}; S_{tot} = \sum_{i=1}^{3}\sum_{j=1}^{3} S_{i,j};$$

$$S_x \sum_{i=1}^{3} S_{i,1}; S_y = \sum_{i=1}^{3} S_{i,2}; S_z = \sum_{i=1}^{3} S_{i,3}; V_{m,n}^{ind} = \begin{bmatrix} v_{11} & v_{12} & v_{13} \\ v_{21} & v_{22} & v_{23} \\ v_{31} & v_{32} & v_{33} \end{bmatrix};$$

and
   $V_{i,j}$ represents the measured values of all orthogonal signal components in the one of the signal sensor arrays.

4. The method according to claim 3, wherein a frequency of each of the orthogonally oriented alternating magnetic fields is below 100 kHz.

5. The method according to claim 3, wherein a signal generator array of the signal generator arrays is identified as actively generating a signal by including an encoded signal in any of the orthogonally oriented alternating magnetic field sequences.

6. The method according to claim 3, wherein a quality of the positions of the signal sensor arrays is verified by comparing all known distances between the signal sensor arrays against calculated distances between the signal sensor arrays from the coordinate data of each of the signal sensor arrays.

7. The method according to claim 2, wherein a frequency of each of the orthogonally oriented alternating magnetic fields is below 100 kHz.

8. The method according to claim 2, wherein a signal generator array of the signal generator arrays is identified as actively generating a signal by including an encoded signal in any of the orthogonally oriented alternating magnetic field sequences.

9. The method according to claim 2, wherein a quality of the positions of the signal sensor arrays is verified by comparing all known distances between the signal sensor arrays against calculated distances between the signal sensor arrays from the coordinate data of each of the signal sensor arrays.

10. The method according to claim 1, wherein the positions of the signal sensor arrays are swapped with positions of the signal generator arrays, and the positions of the signal generator arrays are swapped with the positions of the signal sensor arrays.

11. The method according to claim 1, wherein each of the signal generator arrays sequentially generates a sequence of orthogonally oriented alternating magnetic fields, and a signal generator array of the signal generator arrays is identified as actively generating a signal by including an encoded signal in any of the orthogonally oriented alternating magnetic field sequences.

12. The method according to claim 1, wherein a quality of the positions of the signal sensor arrays is verified by comparing all known distances between the signal sensor arrays against calculated distances between the signal sensor arrays from the coordinate data of each of the signal sensor arrays.

13. The method according to claim 1, further comprising:
   calculating a center of the portable image detector assembly, and
   calculating a source to image receptor distance based on a distance between the calculated center of the portable image detector assembly and the emission point of the X-ray source.

14. A system for determining a relative position of a portable image detector assembly with respect to an emission point of an X-ray source in a radiographic system, the system comprising:
   a set of at least three spatially distributed signal generator arrays that are with physically connected to the emission point of the X-ray source, and that sequentially generate signals, each of the signal generator arrays comprising a triplet of orthogonally arranged coils;
   a set of at least three signal sensor arrays that are physically connected to the portable image detector assembly, and that simultaneously measure the sequentially generated signals, each of the signal sensor arrays comprising a triplet of orthogonally arranged coils;
   a processor configured or programmed to calculate absolute distances between each of the signal generator arrays and each of the signal sensor arrays, respectively, based on the measured sequentially generated signals; and
   a processor configured or programmed to calculate coordinate data for a position of each of the signal sensor arrays by performing trilateration on the absolute distances between the signal generator arrays and signal sensor arrays, respectively.

* * * * *